United States Patent [19]

Nimry

[11] Patent Number: 4,654,456

[45] Date of Patent: Mar. 31, 1987

[54] AMS-1B CRYSTALLINE BOROSILICATE MOLECULAR SIEVE-BASED CATALYST COMPOSITIONS AND PROCESS FOR XYLENE ISOMERIZATION

[75] Inventor: Tayseer S. Nimry, Glen Ellyn, Ill.

[73] Assignee: Amoco Corporation, Chicago, Ill.

[21] Appl. No.: 801,470

[22] Filed: Nov. 25, 1985

[51] Int. Cl.[4] ............................................. C07C 5/22
[52] U.S. Cl. ..................................... 585/477; 585/481
[58] Field of Search ............................. 585/477, 481

[56] References Cited

U.S. PATENT DOCUMENTS 4,268,420  5/1981  Klotz .................................... 585/486

Primary Examiner—Curtis R. Davis
Attorney, Agent, or Firm—Reed F. Riley; William T. McClain; William H. Magidson

[57] ABSTRACT

An improved catalyst composition for isomerizing xylene containing a minor amount of ethylbenzene comprising a HAMS-1B crystalline borosilicate molecular sieve incorporated into an inorganic matrix impregnated with a small amount of a phosphorus compound. The catalyst composition when contacted with an ethylbenzene containing xylene under isomerization conditions results in a greater yield of paraxylene and a conversion of ethylbenzene to more useful products.

6 Claims, No Drawings

AMS-1B CRYSTALLINE BOROSILICATE MOLECULAR SIEVE-BASED CATALYST COMPOSITIONS AND PROCESS FOR XYLENE ISOMERIZATION

BACKGROUND OF THE INVENTION

This invention relates to improved AMS-1B crystalline molecular sieve-based catalyst compositions, and particularly, to the use of such compositions having improved ability to selectively isomerize xylene feeds.

In U.S. Pat. No. 4,532,226, a ZSM-5 aluminosilicate zeolite catalyst modified by P and Cr, Mo, or W and used to selectively catalyze formation of the 1,4-dialkyl isomer during conversion of aromatic compounds is described. U.S. Pat. No. 4,518,703 teaches a P modified silica polymorph-based catalyst for the methylation of toluene. In U.S. Pat. Nos. 4,504,690, 4,128,592 and 4,086,287 is taught modifying a ZSM-5 aluminosilicate zeolite catalyst with P, Mg or P/Mg oxides to obtain high proportions of the 1,4-dialkyl isomer. Phosphorus modification of a ZSM-5 zeolite catalyst for the alkylation of toluene to form a higher proportion of p-xylene is shown in J. Appl. Polymer Sci. 36, 209 (1981) as are P or Mg modified ZSM-5 zeolite catalysts for the disproportionation of toluene. Selective para-alkylation using P modified ZSM-5 zeolite catalysts is again described in J. Cat. 67, 159 (1981). Conversion of olefins over the same type of catalyst is shown in J. Cat. 61, 155 (1980). Disproportionation of toluene to produce benzene and xylenes over P/Mg modified crystalline aluminosilicate zeolite catalysts is described in U.S. Pat. No. 4,137,195. Alkylation or disproportionation of certain monosubstituted benzene compounds to achieve nearly 100% selectivity to para-disubstituted derivatives over phosphorus compound-modified ZSM-5 aluminosilicate zeolite catalysts is reported in J. Am. Chem. Soc. 101, 6783 (1979).

Use of Mg compounds alone or in combination with P compounds to modify a ZSM-5 aluminosilicate of zeolite catalyst is described in U.S. Pat. No. 4,049,573 and the modified catalyst is used for converting alcohols and ethers to hydrocarbons. Again, magnesium is used to modify ZSM-5 zeolite catalysts in U.S. Pat. No. 4,002,698, which catalysts can be used for the selective production of p-xylene from charge stocks of toluene and a $C_3$–$C_{10}$ olefin; P modified catalysts for the methylation of toluene are also described. Phosphorus modified ZSM-5 aluminosilicate zeolite catalysts are again described in U.S. Pat. No. 3,972,832 and described as useful for the conversion of aliphatics to various products.

Catalyst compositions, generally useful for hydrocarbon conversion, based upon AMS-1B crystalline borosilicate molecular sieve have been described in U.S. Pat. Nos. 4,268,420, 4,269,813, 4,285,919 and Published European Application No. 68,796.

As described in the references in the paragraph above, catalyst compositions typically are formed by incorporating an AMS-1B crystalline borosilicate molecular sieve material into a matrix such as alumina, silica or silica-alumina to produce a catalyst formulation. In one method of making AMS-1B crystalline borosilicate, sieve is formed by crystallizing sources for silicon oxide and boron oxide with sodium hydroxide and an organic compound. After crystallization, the resulting sodium form is ion exchanged with an ammonium compound and calcined to yield the hydrogen form of AMS-1B. In another more preferred method, AMS-1B crystalline borosilicate is crystallized in the hydrogen form from a mixture containing a diamine in place of a metal hydroxide. AMS-1B borosilicates in hydrogen form are designated HAMS-1B. Typically, the hydrogen form sieve is gelled with an alumina sol, dried and calcined to yield a catalyst composition.

SUMMARY OF THE INVENTION

An improved catalyst composition having superior xylene isomerization properties and a process for the use of such compositions which improves conversion of the ethylbenzene in ethylbenzene-containing xylene streams to more useful products and improves paraxylene production, comprising a HAMS-1B crystalline borosilicate molecular sieve incorporated into a matrix which has been impregnated with a small amount of a phosphorus compound and its use for isomerizing an ethylbenzene-containing xylene.

DETAILED DESCRIPTION OF THE INVENTION

The catalyst composition of this invention comprises an AMS-1B crystalline borosilicate molecular sieve incorporated into a matrix and impregnated with a solution containing a suitable phosphorus salt, which impregnated catalyst composition is then dried and calcined. Described also is a process for using these impregnated catalyst compositions for the isomerization of a xylene which contains a minor amount of ethylbenzene to produce larger yields of paraxylene and more useful ethylbenzene reaction products.

The form of the AMS-1B crystalline borosilicate molecular sieve which is incorporated with the inorganic matrix is the hydrogen form, i.e., HAMS-1B. This catalyst composition is then impregnated with a phosphorus compound as set forth below.

Phosphorus can be incorporated into such catalyst compositions substantially in the form of phosphorus oxide in an amount from about 0.5% to about 25% phosphorus by weight, preferably about 1% to about 15% by weight phosphorus. Such incorporation can be readily effected by contacting the catalyst composition with a solution of a suitable phosphorus compound, followed by removal of the solvent by drying and finally calcining the dried mass to convert the phosphorus in the composition substantially to its oxide form.

Preferred phosphorus-containing compounds include diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate and other alcohol-$P_2O_5$ reaction products. Particularly preferred are phosphoric acid, triethylphosphite and ammonium phosphates, including ammonium hydrogen phosphate, $(NH_4)_2HPO_4$, and ammonium dihydrogen phosphate, $NH_4H_2PO_4$.

Solvents for use in the impregnation step which can be by means of incipient impregnation or otherwise are polar or non-polar solvents including water and organic solvents. More preferably, they include water and organic solvents such as hydrocarbons and alcohols. Importantly, the solvent should not react with the catalyst compositions in a way destructive of their catalytic capability.

The temperature used in the impregnation step is generally that required to air evaporate the solvent or less, i.e., up to about 150° C. High temperatures during the solvent removal step, i.e., drying, are generally to be avoided.

Calcination is generally conducted in the presence of air at a temperature of between about 350° C. and about 650° C. Temperatures from about 400° C. up to about 600° C. are preferred. Such calcination is generally carried out for 3 to 10 hours but may be extended to 24 hours or longer. Care should be taken to avoid catalyst composition degradation during calcination. After calcination the phosphorus is substantially in the oxide form.

The catalyst compositions used in this invention are based on AMS-1B crystalline borosilicate molecular sieve, which is described in U.S. Pat. Nos. 4,268,420, 4,269,813, and 4,285,919 and Published European Patent Application No. 68,796, all incorporated herein by reference. AMS-1B crystalline borosilicate generally can be characterized by the X-ray pattern listed in Table A and by the composition formula:

$0.9 \pm 0.2 M_{2/n}O:B_2O_3:ySiO_2:zH_2O$ wherein M is at least one cation, n is the oxidation state of the cation, y is between 4 and about 600 and z is between 0 and about 160.

TABLE A

| d-Spacing Å (1) | Assigned Strength (2) |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

(1) Copper K alpha radiation
(2) VW = very weak;
W = weak;
M = medium;
MS = medium strong;
VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mol ratios of the various reactants can be varied to produce the crystalline borosilicates of this invention. Specifically, the mol ratios of the initial reactant concentrations are indicated below:

| | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01–11 | 0.1–2 | 0.1–1 |
| $H_2O/OH^-$ | 10–4000 | 10–500 | 10–500 | wherein R is an organic compound and M is at least one cation having the oxidation state n, such as an alkali or an alkaline earth metal cation or hydrogen. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a base, a boron oxide source, and an organic template compound in water (preferably distilled or deionized). The order of addition usually is not critical, although a typical procedure is to dissolve base and boric acid in water and then add the template compound. Generally, the silicon oxide compound is added with intensive mixing such as that performed in a Waring Blendor and the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of materials affording silicon oxide useful in this invention include silicic acid, sodium silicate, tetraalkyl silicates and Ludox, a stabilized polymer of silicic acid manufactured by E. I. DuPont de Nemours & Co. Typically, the oxide of boron source is boric acid although equivalent species can be used such as sodium borate and other boron-containing compounds.

Cations useful in formation of AMS-1B crystalline borosilicate include alkali metal and alkaline earth metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation hydroxides with an organic base such as ethylenediamine as described in Published European Application No. 68,796.

Organic templates useful in preparing AMS-1B crystalline borosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about 11.0±0.2 using a compatible acid or base such as sodium bisulfate or sodium hydroxide. After sufficient quantities of a silica source such as a silicic acid polymer (Ludox) are added with intensive mixing, preferably the pH is again checked and adjusted to a range of about 11.0±0.2.

Alternatively, AMS-1B crystalline borosilicate molecular sieve can be prepared by crystallizing a mixture of sources for an oxide of silicon, an oxide of boron, an alkyl ammonium compound and ethylenediamine such that the initial reactant molar ratios of water to silica range from about 5 to about 25, preferably about 5 to about 20 and most preferably from about 10 to about 15. In addition, preferable molar ratios for initial reactant silica to oxide of boron range from about 4 to about 150, more preferably from about 5 to about 80 and most preferably from about 5 to about 20. The molar ratio of ethylenediamine to silicon oxide should be about above about 0.05, typically below 5, preferably between about 0.1 and about 1.0 and most preferably between about 0.2 and 0.5. The molar ratio of alkylammonium compound, such as tetra-n-propylammonium bromide, to silicon oxide can range from 0 to about 1 or above, typically above about 0.005, preferably about 0.01 to about 0.1, more preferably about 0.01 to about 0.08 and, most preferably, about 0.02 to about 0.05.

The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about one to about seven days, at a temperature ranging from about 100° C. to about 250° C., preferably about 125° C. to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50°–225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° C. to about 850° C. and preferably about 425° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure, either before or after incorporation into a matrix, by ion exchange, impregnation, a combination thereof, or other suitable contact means. Before placing a catalytically active metal ion or compound on the borosilicate structure, the borosilicate should be in the hydrogen form. If the sieve was prepared using a metal hydroxide, such as sodium hydroxide, the hydrogen form typically is produced by exchange one or more times with ammonium ion, typically using ammonium acetate, followed by drying and calcination as described above.

The original cation in the AMS-1B crystalline borosilicate can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for hydrocarbon conversion. Typical catalytically active ions include hydrogen, metal ions of Groups IB, IIA, IIB, IIIA, VB, VIB and VIII, and of manganese, vanadium, chromium uranium, and rare earth elements.

Also, water soluble salts of catalytically active materials can be impregnated onto the crystalline borosilicate of this invention. Such catalytically active materials include metals of Groups IB, IIA, IIB, IIIA, IIIB, IVB, VB, VIB, VIIB, and VIII, and rare earth elements.

Examples of catalytically active elements include ruthenium, rhodium, iron, cobalt, and nickel. Mixtures of elements can be used. Other catalytic materials include ions and compounds of aluminum, lanthanum, molybdenum, tungsten, and noble metals such as ruthenium, osmium, rhodium, iridium, palladium, and platinum. Other additional catalytic materials can be ions and compounds of scandium, yttrium, titanium, zirconium, hafnium, vanadium, niobium, tantalum, chromium, cerium, manganese, cobalt, iron, zinc, and cadmium. Specific combinations of non-noble metals of Group VIII and other catalytic materials include ions or compounds of nickel and osmium, nickel and lanthanum, nickel and palladium, nickel and iridium, nickel and molybdenum, and nickel and tungsten.

Ion exchange and impregnation techniques are well-known in the art. Typically, an aqueous solution of a cationic species is exchanged one or more times at about 25° C. to about 100° C. A hydrocarbon-soluble metal compound such as a metal carbonyl also can be used to place a catalytically active material. Impregnation of a catalytically active compound on the borosilicate or on a composition comprising the crystalline borosilicate suspended in and distributed throughout a matrix of a support material, such as porous refractory inorganic oxide such as alumina, often results in a suitable catalytic composition. A combination of ion exchange and impregnation can be used. Presence of sodium ion in a composition usually is detrimental to catalytic activity.

The amount of catalytically active material placed on the AMS-1B borosilicate can vary from about 0.01 weight percent to about 30 weight percent, typically from about 0.05 to about 25 weight percent, depending on the process use intended. The optimum amount can be determined easily by routine experimentation.

The AMS-1B crystalline borosilicate useful in this invention is admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina, alumina, magnesia, titania, zirconia, alumina sols, hydrated aluminas, clays such as bentonite or kaolin, or other binders well-known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. The crystalline borosilicate content can vary anywhere from a few up to 100 wt. % of the total composition. Catalytic compositions can contain about 0.1 wt. % to about 100 wt. % crystalline borosilicate material and preferably contain about 10 wt. % to about 95 wt. % of such material and most preferably contain about 20 wt. % to about 80 wt. % of such material.

Catalyst compositions impregnated with a phosphorus compound according to this invention can be in powder form or already in extrudate form.

The xylene feed to the isomerization stage containing the catalyst compositions of the instant invention may be a mixture of ortho, para, and metaxylene, or any of the isomers individually. The feed preferably contains between about 5% and about 25% by weight of ethylbenzene, more preferably about 8% to about 20% ethylbenzene and, most preferably, about 10% to about 15% ethylbenzene. Isomerization conditions can vary considerably but preferably range between a pressure of about 10 psig and about 500 psig and a temperature of about 50° C. to about 500° C., more preferably, between about 100° C. to about 375° C. at pressures from about 20 psig and about 300 psig.

The following Examples will serve to illustrate certain specific embodiments of the hereindisclosed invention. These Examples should not, however, be construed as limiting the scope of the novel invention as there are many variations which may be made thereon without departing from the spirit of the disclosed invention, as those of skill in the art will recognize.

COMPARATIVE EXAMPLE 1

This catalyst composition was made from 40% HAMS-1B crystalline borosilicate sieve and 60% alumina. A 118 g portion of HAMS-1B was gelled with an 1810 g portion of PHF alumina sol that has a 9.47% by weight content of alumina, using 171 ml of concentrated ammonium hydroxide (29% $NH_3$) and 236 g of water. The gel was dried at 165° C. for 18 hours. The dried sample was ground to 18–40 mesh then calcined at 538° C. for 12 hours.

Ten grams of the catalyst was tested for xylene isomerization/ethylbenzene conversion. The catalyst was placed in a ½" i.d. reactor and treated with helium at 250 psig for 2 hours at room temperature. The reactor temperature was then increased to 360° C. under a hydrogen flow and the catalyst was treated with hydrogen at this temperature and other reaction conditions listed in the Table for two more hours. The hydrocarbon feed was then passed through the reactor once-through. The results are also shown in the Table following Example 15.

A typical composition of the feed used in all the hydrocarbon conversion Examples is the following:

| COMPONENT | WT. % |
|---|---|
| Paraffins and Naphthenes (P and N) | 1.960 |
| Benzene (BZ) | — |
| Toluene (Tol) | 0.654 |
| Ethylbenzene (EB) | 15.703 |
| p-xylene (PX) | 7.623 |
| m-xylene (MX) | 48.524 |
| o-xylene (OX) | 21.458 |
| Methylethylbenzene (MEB) | 0.784 |
| Trimethylbenzene (TMB) | 0.519 |
| Diethylbenzene (DEB) | 1.534 |
| Dimethylethylbenzene (DMEB) | 1.420 |
| Tetramethylbenzene (TTMB) | 0.045 |

EXAMPLE 2

In a small beaker containing 38 g of water was dissolved 3.2 g of $(NH_4)_2HPO_4$. The solution was then added slowly to 25 g of the catalyst of Example 1 while stirring with a glass rod. The sample was then dried at 130° C. for 16 hours and calcined at 538° C. for 12 hours. The resulting impregnated catalyst composition contained approximately 2.7 weight percent phosphorus.

EXAMPLE 3

The catalyst composition of Example 3 was tested for isomerization as in Example 1. The reaction conditions and the results are shown in the Table.

EXAMPLE 4

An impregnated catalyst composition was prepared as in Example 2 by using 25 g of the catalyst composition of Example 1 and 5.33 g of $(NH_4)_2HPO_4$. The resulting catalyst composition contained approximately 4.2% by weight phosphorus.

EXAMPLE 5

The catalyst composition of Example 4 was tested for isomerization as in Example 1. The reaction conditions and results are shown in the Table.

EXAMPLE 6

An impregnated catalyst composition was prepared as in Example 2 by using 25 g of the catalyst composition of Example 1 and 10.66 g of $(NH_4)_2HOP_4$. The amount of phosphorus in this catalyst composition was approximately 7.6% by weight.

EXAMPLE 7

The catalyst composition of Example 6 was tested as in Example 1. The reaction conditions and results are shown in the Table.

EXAMPLE 8

An impregnated catalyst composition was prepared as in Example 2 by using 25 g of the catalyst composition of Example 1 and 9.29 g of $NH_4H_2PO_4$. The resulting catalyst composition contained approximately 7.8% by weight phosphorus.

EXAMPLE 9

The catalyst composition of Example 8 was tested as in Example 1. The reaction conditions and results are shown in the Table.

EXAMPLE 10

An impregnated catalyst composition was prepared by adding a methanol solution of triethylphosphite [4.02 g of $(C_2H_5O)_3P$ in 25 g of methanol] to 25 g of the catalyst composition of Example 1 and mixing with a glass rod for a few minutes. The methanol was allowed to evaporate in the hood at room temperature. The sample was then dried at 130° C. for 16 hours then calcined at 538° C. for 12 hours. The resulting catalyst composition contained approximately 2.5% by weight phosphorus.

EXAMPLE 11

The catalyst composition of Example 10 was tested as in Example 1. The reaction conditions and results are shown in the Table.

EXAMPLE 12

An impregnated catalyst composition was prepared by adding 2.37 g of $H_3PO_4$ (85%) in 38 g of water to 25 g of the catalyst composition of Example 1 and stirring with a glass rod for a few minutes. The sample was then dried at 130° C. for 16 hours and calcined at 538° C. for 12 hours. The resulting catalyst composition contained approximately 2.5% by weight phosphorus.

EXAMPLE 13

The catalyst composition of Example 12 was tested as in Example 1. The reaction conditions and results are shown in the Table.

EXAMPLE 14

An impregnated catalyst composition was prepared as in Example 12 by using 3.96 g of $H_3PO_4$ (85%) and of 25 g of the catalyst composition of Example 1. The resulting catalyst composition contained approximately 3.7% by weight phosphorus.

EXAMPLE 15

The catalyst composition of Example 14 was tested as in Example 1. The reaction conditions and results are shown in the Table.

TABLE

| Catalyst Composition of Example | 1 | 3 | 5 | 7 | 9 | 11 | 13 | 15 |
|---|---|---|---|---|---|---|---|---|
| Reactor Temp., °C. | 360.5 | 360 | 360 | 360 | 360.5 | 360.5 | 359 | 360 |
| Reactor Pres., psig | 250 | 250 | 250 | 250 | 250 | 250 | 250 | 250 |
| $H_2$ Flow, ft$^3$/hr. | 1.21 | 1.15 | 1.16 | 1.15 | 1.18 | 1.24 | 1.21 | 1.18 |
| Feed Rate, g/min. | 1.19 | 1.17 | 1.20 | 1.19 | 1.18 | 1.18 | 1.19 | 1.18 |
| $H_2$/Feed Ratio | 2.05 | 1.97 | 1.96 | 1.91 | 2.01 | 2.10 | 2.04 | 2.03 |
| Contact Time, Sec. | 16.0 | 14.49 | 13.21 | 11.18 | 11.71 | 14.47 | 14.53 | 13.63 |
| LWHSV, hr$^{-1}$ | 7.12 | 7.01 | 7.18 | 7.16 | 7.06 | 7.06 | 7.15 | 7.10 |
| Time on Oil, hr. | 20.0 | 20.0 | 20.0 | 20.0 | 20.0 | 20.0 | 20.0 | 20.0 |
| EB Conv., wt. % | 26.93 | 24.13 | 25.57 | 25.50 | 26.13 | 22.81 | 24.12 | 22.61 |
| Xylene Loss, wt. % | 5.04 | 3.77 | 3.96 | 2.98 | 3.51 | 3.69 | 3.88 | 3.63 |
| EB Conv./Xylene Loss | 5.35 | 6.39 | 6.46 | 8.56 | 7.45 | 6.18 | 6.22 | 6.23 |
| PX PATE, % | 102.35 | 101.93 | 103.18 | 101.77 | 102.07 | 103.11 | 102.25 | 102.37 |
| MX PATE, % | 92.08 | 91.33 | 85.23 | 96.04 | 93.58 | 93.25 | 91.46 | 91.36 |
| OX PATE, % | 126.22 | 125.41 | 111.56 | 114.34 | 120.61 | 125.21 | 127.42 | 127.09 |
| Benzene/Toluene | 2.60 | 2.30 | 2.24 | 2.18 | 2.10 | 2.64 | 2.55 | 2.60 |
| EB Conv. via Disp. 2EB → DEB + BZ | 24.79 | 34.72 | 40.41 | 44.90 | 41.83 | 32.58 | 31.56 | 28.51 |

PATE represents percent approach to equilibrium

What is claimed is:

1. A process for isomerizing a xylene feed containing a minor amount of ethylbenzene comprising contacting said xylene with a catalyst composition comprising a HAMS-1B crystalline borosilicate molecular sieve incorporated into an inorganic matrix, said composition impregnated with a suitable phosphorus compound and subsequently heated to substantially convert said compound to the oxide form.

2. The process of claim 1 wherein said phosphorus compound is ammonium hydrogen phosphate, ammonium dihydrogen phosphate, triethylphosphite, or phosphoric acid.

3. The process of claim 2, wherein said catalyst composition contains between about 0.5 and about 25% phosphorus by weight.

4. The process of claim 2 wherein said catalyst composition contains between about 1 and about 15% by weight phosphorus.

5. The process of claim 3 wherein said HAMS-1B molecular sieve comprises from about 20 to about 80 wt. % incorporated into an alumina, silica, or silica-alumina matrix.

6. The process of claim 4 wherein said HAMS-1B molecular sieve comprises from about 20 to about 80 wt. % incorporated into an alumina, silica, or silica-alumina matrix.

* * * * *